United States Patent
Li et al.

(10) Patent No.: US 9,867,764 B2
(45) Date of Patent: *Jan. 16, 2018

(54) ORAL CARE COMPOSITION

(71) Applicant: Conopco, Inc., Englewood Cliffs, NJ (US)

(72) Inventors: Xiaoke Li, Shanghai (CN); Weining Liu, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/914,120

(22) PCT Filed: Sep. 2, 2014

(86) PCT No.: PCT/EP2014/068560
§ 371 (c)(1),
(2) Date: Feb. 24, 2016

(87) PCT Pub. No.: WO2015/036277
PCT Pub. Date: Mar. 19, 2015

(65) Prior Publication Data
US 2016/0206525 A1  Jul. 21, 2016

(30) Foreign Application Priority Data

Sep. 10, 2013  (CN) .................. PCT/CN2013/083240
Oct. 14, 2013  (EP) ..................................... 13188474

(51) Int. Cl.
| | | |
|---|---|---|
| *A61Q 11/00* | (2006.01) | |
| *A61K 8/25* | (2006.01) | |
| *A61K 8/29* | (2006.01) | |
| *A61K 9/14* | (2006.01) | |
| *A61K 8/02* | (2006.01) | |

(52) U.S. Cl.
CPC .............. *A61K 8/25* (2013.01); *A61K 8/0241* (2013.01); *A61K 8/29* (2013.01); *A61Q 11/00* (2013.01); *A61K 2800/621* (2013.01); *A61K 2800/651* (2013.01)

(58) Field of Classification Search
CPC .......... A61K 8/0241; A61K 8/25; A61K 8/29; A61Q 11/00
See application file for complete search history.

(56) References Cited

U.S. PATENT DOCUMENTS

| 2006/0225609 A1 | 10/2006 | Rueger et al. |
|---|---|---|
| 2008/0152599 A1 | 6/2008 | Brignoli et al. |
| 2010/0136067 A1 | 6/2010 | Butler et al. |
| 2011/0171145 A1 | 7/2011 | Caldwell |
| 2012/0141588 A1 | 6/2012 | Chopra et al. |

FOREIGN PATENT DOCUMENTS

| EP | 0710475 | 11/2001 |
|---|---|---|
| EP | 1550428 | 3/2009 |
| WO | WO2005117806 | 12/2005 |
| WO | WO2007140897 | 12/2007 |
| WO | WO2008015117 | 2/2008 |
| WO | WO2008068149 | 6/2008 |
| WO | WO2008068248 | 6/2008 |
| WO | WO2009023353 | 2/2009 |
| WO | WO2010054494 | 5/2010 |
| WO | WO2011109919 | 9/2011 |
| WO | WO2012031785 | 3/2012 |
| WO | WO2012031786 | 3/2012 |
| WO | WO2012078136 | 6/2012 |

OTHER PUBLICATIONS

Wu et al. Hierachically Nanostructured Mesoporous Spheres of Calcium Silicate Hydrate: Surfactant-free Sonochemical Synthesis and Drug-Delivery System with Ultrahigh Drug-loading Capacity. (2010) Adv. Mater. vol. 22. pp. 749-753.*
Taylor, H.F.W. Hydrated Calcium Silicates. Part V. The Water Content of Calcium Silicate Hydrate. Jan. 1, 1953. pp. 163-171.*
IPRP2 in PCTEP2014068604, dated Dec. 18, 2015 (NPL 1, pp. 1-19).
Search Report and Written Opinion in EP13188473, dated Apr. 7, 2014 (NPL 1, pp. 20-27).
Search Report and Written Opinion in EP13188474, dated Apr. 8, 2014 (NPL 1, pp. 28-36).
Search Report and Written Opinion in PCTEP2014068560, dated Nov. 24, 2014 (NPL 1, pp. 37-48).
Search Report in PCTEP2014068604, dated Jan. 30, 2015 (NPL 1., pp. 49-53).
Written Opinion in PCTEP2014068604, dated Jan. 30, 2015 (NPL 1, pp. 54-59).
Co-pending application, Li et al., Filed Feb. 24, 2016.
Dr. Balaji D. More, Physical sunscreens: On the comeback trail, Indian J Dermatol Venereol Leprol, 2007, pp. 30-85, vol. 73 Issue 2.
Rommens et al., Keeping on the White track, European Coatings Journal, 2015, pp. 88-92www.european-coatings.com.
Toedt et al., Chemical Compositions of Everyday Products, Chemistry Analytic, 2005, pp. 60-62, ., Greenwood Press.

* cited by examiner

Primary Examiner — Tracy Liu
(74) Attorney, Agent, or Firm — Foley & Lardner LLP

(57) ABSTRACT

An oral care composition is disclosed comprising calcium silicate and high refractive index composite particles, wherein the refractive index of the composite particles is in the range from 1.9 to 4.0, and wherein the calcium silicate and high refractive index composite particles are present at a calcium silicate to composite particles weight ratio of 1:10 to 2:1.

17 Claims, No Drawings

ORAL CARE COMPOSITION

TECHNICAL FIELD OF THE INVENTION

The present invention relates to oral care compositions such as tooth pastes, gums, mouthwashes and the like. In particular the present invention relates to oral care compositions containing a particulate tooth whitening agent. The invention also relates to the use of such compositions for whitening and/or remineralizing of teeth of an individual.

BACKGROUND OF THE INVENTION

The enamel layer of the tooth is naturally an opaque white or slightly off-white colour. However, this enamel layer can become stained or discoloured. The enamel layer of the tooth is composed of hydroxyapatite mineral crystals that create a somewhat porous surface. It is believed that this porous nature of the enamel layer allows staining agents and discolouring substances to permeate the enamel and discolour the tooth.

Many products we consume have a negative impact on our teeth and mouth. Many substances can stain or reduce the whiteness of one's teeth, in particular, certain foods, tobacco products, and fluids such as tea and coffee. These staining and discolouring substances are often able to permeate the enamel layer. This problem occurs gradually over many years, but imparts a noticeable discoloration of the enamel of one's teeth.

Consumers have always had a strong desire for white teeth and many individuals are dissatisfied with their current teeth colour. This desire for whiter teeth has given rise to a growing trend in the increased use of tooth whitening products.

A variety of products are currently used for teeth whitening. Such products often comprise peroxides, abrasives or both in order to clean and whiten teeth. These types of products are often not desired since they do not contribute to the remineralization of teeth and can cause damage to teeth and gums if overused. Products comprising calcium source have been developed in an attempt to enhance the characteristics of teeth. Such products, however, do not positively adhere to teeth and thereby may only contact teeth for a brief period of time prior to being rinsed out of the mouth in wash water.

The present inventors have now recognized a need to develop an oral care product which has tooth whitening agents that are suitable to adhere to the surface of teeth for a long enough period of time to provide not only instant but also long-lasting whitening benefits to teeth. It has been found that calcium silicate, especially calcium silicate in the form of a hydrate can behave as a deposition aid and unexpectedly enhances the deposition of particulate tooth whitening agent on tooth surfaces which delivers both instant and excellent long-lasting tooth whitening benefits.

Additional Information

WO 2008/068149 A (Unilever) discloses an oral care product comprising a first composition comprising an insoluble calcium salt that is not a calcium phosphate salt, a second independent composition comprising a source of phosphate ions, and a means for delivering each of the compositions to the surface of the teeth. The preferred insoluble calcium salt is calcium silicate.

WO 2008/015117 A (Unilever) discloses a calcium oxide-silica composite biomaterial either in amorphous state or crystalline state having an average pore size, as determined by the BET method, in the range of from 0.8 to 4 nm, wherein the calcium oxide-silica content of the biomaterial is at least 80 wt percent, the balance being optionally one or more other materials and wherein the molar ratio of calcium oxide to silica is at least 0.1.

WO 2012/031785 A (Unilever) discloses composite particle actives suitable for use in oral care compositions. The composite particle actives have a core and a coating whereby the coating interacts with phosphate ions to produce calcium and phosphate reaction products that are suitable to adhere to tooth enamel and/or dentin in order to improve characteristics of teeth.

WO 2012/031786 A (Unilever) discloses oral care compositions with composite particle actives described in WO 2012/031785 A (Unilever).

None of the additional information above describes an oral care composition comprising calcium silicate, particularly calcium silicate hydrate as a deposition aid which enhances the deposition of particulate whitening agents on teeth surface in order to achieve excellent instant and long-lasting tooth whitening results.

Tests and Definitions

Dentifrice

"Dentifrice" for the purposes of the present invention means a paste, powder, liquid, gum or other preparation for cleaning the teeth or other surfaces in the oral cavity.

Tooth Paste

"Tooth paste" for the purpose of the present invention means a paste or gel dentifrice for use with a toothbrush. Especially preferred are tooth pastes suitable for cleaning teeth by brushing for about two minutes.

Mouth Wash

"Mouth wash" for the purpose of the present invention means liquid dentifrice for use in rinsing the mouth. Especially preferred are mouth washes suitable for rinsing the mouth by swishing and/or gargling for about half a minute before expectorating.

Particle Size

"Particle size", as used herein, refers to particle diameter unless otherwise stated. Diameter is meant to mean the largest measurable distance on a particle in the event a well-defined sphere is not generated. Particle size can be measured, for example, by dynamic light scattering (DLS).

Composite Particle

"Composite particle", as used herein, refers to a particle comprising a first component core and a second component coating wherein the core and coating are composed of different materials.

Refractive Index

Refractive index is quoted at a temperature of 25° C. and a wavelength of 589 nm.

pH pH is quoted at atmospheric pressure and a temperature of 25° C. When referring to the pH of an oral care composition, this means the pH measured when 5 parts by weight of the composition is uniformly dispersed and/or dissolved in 20 parts by weight pure water at 25° C. In particular the pH may be measured by manually mixing 5 g oral care composition with 20 mL water for 30 s, then immediately testing the pH with indicator or a pH meter.

Solubility

"Soluble" and "insoluble", as used herein, refers to the solubility of a source (e.g., like calcium salts) in water at 25° C. and atmospheric pressure. "Soluble" means a source that dissolves in water to give a solution with a concentration of at least 0.1 moles per liter. "Insoluble" means a source that dissolves in water to give a solution with a concentration of less than 0.001 moles per liter. "Sparingly soluble", therefore, is defined to mean a source that dissolves in water to give a solution with a concentration of greater than 0.001 moles per liter and less than 0.1 moles per liter.

Water of Hydration

"Water of hydration", as used herein, refers to water chemically combined with a substance in a way that it can be removed by heating without substantially changing the chemical composition of the substance. In particular, water which could only be removed when heated above 200° C. The water loss is measured using thermo gravimetric analysis (TGA) with a Netzsch TG instrument. The TGA is conducted under an $N_2$ atmosphere with heating rate of 10 degree/min in the range of 30 to 900° C.

Substantially Free

"Substantially free of", as used herein, means less than 1.5%, and preferably less than 1.0%, and more preferably less than 0.75% and more preferably still less than 0.5%, and even more preferably less than 0.1% and most preferably from 0.0 to 0.01% by weight, based on total weight of the oral care composition, including all ranges subsumed therein.

Viscosity

Viscosity of a tooth paste is the value taken at room temperature (25° C.) with a Brookfield Viscometer, Spindle No. 4 and at a speed of 5 rpm. Values are quoted in centipoises (cP=mPa·S) unless otherwise specified.

Remineralization

"Remineralization", as used herein, means in situ (i.e. in the oral cavity) generation of calcium phosphate on teeth (including layers on teeth from 10 nm to 20 microns, and preferably from 75 nm to 10 microns, and most preferably, from 150 nm to 5 microns thick including all ranges subsumed therein) to reduce the likelihood of tooth sensitivity, tooth decay, regenerate enamel and/or improve the appearance of teeth by whitening through the generation of such new calcium phosphate.

Miscellaneous

Except in the examples, or where otherwise explicitly indicated, all numbers in this description indicating amounts of material or conditions of reaction, physical properties of materials and/or use may optionally be understood as modified by the word "about".

All amounts are by weight of the final oral care composition, unless otherwise specified.

It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

SUMMARY OF THE INVENTION

In a first aspect, the present invention is directed to an oral care composition comprising:

a) calcium silicate; and
b) high refractive index composite particles
wherein the calcium silicate and high refractive index composite particles are present in a weight ratio (a:b) of 1:10 to 2:1.

In a second aspect, the present invention is directed to a packaged oral care product comprising the oral care composition of the first aspect of this invention.

In a third aspect, the present invention is directed to a process for manufacturing any embodiment of the oral care composition of the first embodiment comprising the steps of:
i) manufacturing high refractive index composite particles;
ii) mixing the composite particles with calcium silicate to form the oral care composition.

In a fourth aspect, the present invention is directed to a method for providing tooth whitening benefits by using oral care composition of the first aspect of this invention.

All other aspects of the present invention will more readily become apparent upon considering the detailed description and examples which follow.

DETAILED DESCRIPTION

Now it has been found that the presence of calcium silicate especially calcium silicate in the form of a hydrate can behave as a deposition aid and unexpectedly enhances the deposition of particulate tooth whitening agent such as high refractive index composite particles on teeth surfaces which delivers not only instant but also excellent long-lasting whitening benefits.

The term "deposition aid" in the context of the present invention generally means a material which aids deposition of the particulate tooth whitening agent from the continuous phase of the composition onto the tooth surface during use of the composition.

Calcium Silicate

In a preferred embodiment, the calcium silicate used is $CaSiO_3$ which has low water solubility and is made commercially available under the name Sorbosil CA40 by PQ. In another preferred embodiment, the calcium silicate is insoluble, present as the composite material calcium oxide-silica ($CaO$—$SiO_2$), which is described, for example, in international patent application published as WO 2008/01517 (Unilever) which is hereby incorporated by reference in its entirety. For a calcium silicate composite material, the atom ratio of calcium to silicon (Ca:Si) may be from 1:10 to 3:1. The Ca:Si ratio is preferably 1:5 to 2:1, and more preferably, from 1:3 to 2:1, and most preferably, from about 1:2 to 2:1. The calcium silicate may comprise mono-calcium silicate, bi-calcium silicate, or tri-calcium silicate. The calcium silicate may be in a crystalline or amorphous state or even in a mesoporous state.

In addition to calcium oxide, silica, the particles comprising the calcium silicate which is not hydrated may comprise other components, such as metal cations, anions (such as phosphate) and the like. However, it is preferred that the particles comprise calcium oxide, silica in an amount of at least 70% by weight of the particles, more preferably at least 80%, more preferably still at least 90% and even more preferably at least 95%. Most preferably the particles consist of (or at least consist essentially of) calcium oxide, silica.

In an especially preferred embodiment, the calcium silicate is calcium silicate hydrate. The calcium silicate hydrate for use in the present invention comprises at least calcium oxide (CaO), silica ($SiO_2$) and water. Compared with conventional calcium silicate which are not hydrated, the calcium silicate hydrate comprises the water of hydration in an amount of at least 5% by weight of the calcium silicate hydrate, preferably at least 10%, more preferably at least 15%, even more preferably at least 20% and most preferably at least 25%. The water content is typically no greater than 50% by weight of the calcium silicate hydrate, more preferably no greater than 40%, even more preferably no greater than 35% and most preferably no greater than 30%.

The calcium silicate hydrate preferably comprises at least 20% silica by weight of the calcium silicate hydrate, more preferably at least 30%, more preferably still at least 40% and most preferably at least 55%. The silica content is preferably no greater than 70% by weight of the calcium silicate hydrate, more preferably no greater than 65% and most preferably no greater than 60%.

To provide calcium necessary for remineralization, the calcium silicate hydrate preferably comprises calcium oxide in an amount of at least 5% by weight of the calcium silicate hydrate, more preferably at least 7%, more preferably still at least 10%, even more preferably at least 12% and most preferably at least 15%. The calcium oxide content is typically no greater than 50% by weight of the calcium silicate hydrate, more preferably no greater than 40%, even more preferably no greater than 30% and most preferably no greater than 25%.

The calcium silicate hydrate preferably comprises Ca and Si in an atom ratio (Ca:Si) less than 1:1, more preferably less than 1:1.2, more preferably still from 1:1.5 to 1:4 and most preferably from 1:1.7 to 1:3.

The calcium silicate may be amorphous or at least partly crystalline or mesoporous. The calcium silicate is preferably particulate as this allows for maximum surface area for contact with dental tissue. Thus preferably the composition comprises particles comprising the calcium silicate. More preferably the particles have a weight average particle size of five microns or less, and even more preferably from 10 to 100%, and especially, from 25 to 100%, and most especially, from 70% to 100% by weight of the particles comprising calcium silicate used in this invention have a particle size from 0.1 to 1.5 microns.

In addition to calcium oxide, silica and water, the particles which comprise the calcium silicate hydrate may comprise other components, such as metal cations, anions (such as phosphate) and the like. However, it is preferred that the particles comprise CaO, $SiO_2$ and water in an amount of at least 70% by weight of the particles, more preferably at least 80%, more preferably still at least 90% and even more preferably at least 95%. Most preferably the particles consist of (or at least consist essentially of) CaO, $SiO_2$ and water.

Typically, the oral care composition of the present invention comprises from 0.1 to 50% by weight of the calcium silicate, more preferably from 0.2 to 30%, most preferably from 1 to 20%, based on the total weight of the oral care composition and including all ranges subsumed therein.

Composite Particles

The only limitation with respect to the composite particle that may be used in this invention is that the same is suitable for use in the mouth.

It is known that the refractive index of a particle comprising more than one material can be calculated based on the refractive indices and volume fractions of the constituents using effective medium theory, as is described for example in WO 2009/023353. In order to provide excellent whitening effect, the composite particles of the present invention is preferred to have a high refractive index of at least 1.9, more preferably at least 2.0, even more preferably at least 2.2, even more preferably still at least 2.4 and most preferably at least 2.5. The maximum refractive index of the composite particles is not particularly limited but preferably up to 4.0.

The composite particle comprises a first component core and a second component coating. Typically, the core of the composite particle comprises a material suitable to physically and immediately improve characteristics of teeth and especially whiten teeth. Particular suitable materials are metal salts and preferred are salts where the metal is selected from zinc (Zn), titanium (Ti), zirconium (Zr) or a combination thereof. Preferably, the metal salts is (or at least comprises) a metal oxide such as titanium dioxide ($TiO_2$), zinc oxide (ZnO), zirconium dioxide ($ZrO_2$) or a combination thereof. In addition, the core of the composite particle can also comprise non-metal oxides such as silicon monoxide (SiO).

The core of the composite particle typically makes up from 3 to 98%, and preferably from 6 to 65%, and most preferably from 10 to 55% by weight of the composite particle, based on total weight of the composite particle and including all ranges subsumed therein. In a preferred embodiment, the core comprises metal oxides, non-metal oxides or a combination thereof in an amount of at least 50% by weight of the core and more preferably at least 70%, more preferably still from 80 to 100% and most preferably from 85 to 95%. In an especially preferred embodiment, the core is at least 50% by weight titanium dioxide, and most preferably, from 60 to 100% by weight titanium dioxide, based on total weight of the first component core.

The second component coating comprises material suitable to adhere to tooth enamel, dentin or both. Typically the coating material comprises the element calcium, and optionally, other metals like potassium, sodium, aluminium, magnesium as well as mixtures thereof whereby such optional metals are provided as, for example, sulphates, lactates, oxides, carbonates or silicates. Optionally, the coating material may be aluminium oxide or silica. In a preferred embodiment, the coating material is suitable to provide a biological or chemical improvement to teeth which is long term (e.g., results in hydroxyapatite formation). Preferably, the coating employed comprises at least 50% by weight elemental calcium, and most preferably, at least 65% by weight elemental calcium based on total weight of metal in the coating. In an especially preferred embodiment, the metal in the coating is from 80 to 100% by weight of elemental calcium, based on total weight of metal in the second component coating and including all ranges subsumed therein. In another especially preferred embodiment, the core and the coating are slightly soluble or insoluble in water, but most preferably, insoluble in water.

Usually, at least 30% of the outer surface area of the first component core is coated with the second component coating, preferably at least 50% of the core is coated with coating, most preferably, from 70 to 100% of the outer surface area of the first component core is coated with the second component coating.

The diameter of the composite particle is often from 10 nm to less than 50 microns, and preferably, from 75 nm to less than 10 microns. In an especially preferred embodiment, the diameter of composite particle active is from 100 nm to 5 microns, including all ranges subsumed therein. In yet another especially preferred embodiment, at least 40%, and preferably, at least 60%, and most preferably, from 75 to 99.5% of the diameter of the composite particle is the result of core, including all ranges subsumed therein.

Typically, the oral care composition of the present invention comprises from 0.25 to 60%, and preferably, from 0.5 to 40%, and most preferably, from 1 to 30% by weight of the composite particles, based on the total weight of the oral care composition and including all ranges subsumed therein.

In an especially desired embodiment, the second component coating can comprise, for example, calcium phosphate, calcium gluconate, calcium oxide, calcium lactate, calcium carbonate, calcium hydroxide, calcium sulphate, calcium carboxymethyl cellulose, calcium alginate, calcium slats of citric acid, calcium silicate, mixture of thereof or the like. In another desired embodiment, the calcium source in the coating will comprise calcium silicate. These compounds are also suitable to include as reagents for calcium sources when making the composite particles of this invention. Similar salts with sodium, magnesium, aluminium and potassium in lieu of calcium may, for example, be used as reagents to provide the anionic portion of the second component coating during particle manufacturing.

In yet, another preferred embodiment, the coating can comprise the element calcium which originates from insoluble calcium silicate, present as the composite material calcium oxide-silica ($CaO$—$SiO_2$) as described in international patent applications published as WO 2008/015117 and WO 2008/068248.

When a calcium silicate composite material is employed as coating, the ratio of calcium to silicon (Ca:Si) may be from 1:10 to 3:1. The Ca:Si ratio is preferably from 1:5 to 2:1, and more preferably, from 1:3 to 2:1, and most preferably, from about 1:2 to 2:1. The calcium silicate may comprise mono-calcium silicate, bi-calcium silicate, or tri-calcium silicate whereby ratios of calcium to silicon (Ca:Si) should be understood to be atom ratios.

The preferred material employed in this invention to deliver calcium and generate second component coating on the composite particle may be in a crystalline or amorphous state. In an often preferred embodiment, the material to deliver calcium for the coating is in a mesoporous state, i.e. the source is a material having pores with diameters from 1 nm to 1 micron. Mesoporous calcium silicate (MCS) is often preferred.

The MCS which may be used in second component coating in this invention can be made by combining a calcium salt (e.g., calcium chloride, calcium carbonate, calcium hydroxide), a silica precursor like silicate (e.g., sodium silicate, potassium silicate, tetraethyl orthosilicate or tetraethyl silicate) and a structure-directing agent to yield a solid suitable for calcinating. A more detailed description of the process that may be conducted to make the MCS suitable for use in this invention is described in the aforementioned international patent application published as WO 2008/015117.

In an often desired embodiment, coating may be formed from $CaO$—$SiO_2$.

The present inventors have found that excellent whitening performance can be achievable even when the calcium silicate is not used in great excess. Relative weight ratio of calcium silicate to high refractive index composite particles may range from 1:10 to 4:1, preferably from 1:5 to 3:1, most preferably from 1:3 to 2:1.

Optional Components

The composite particles of the present invention may be capable of adhering to tooth surfaces in the presence of calcium silicate even without inclusion of a phosphate source in the oral care composition itself. Without wishing to be bound by theory the present inventors believe that this may be because the calcium silicate in the oral composition of the present invention reacts with phosphate ions in saliva and/or Si—OH groups may have an affinity for Ca ions in teeth. The remineralisation of calcium silicate around the composite particles helps the deposition of composite particles on tooth surface by enhancing their resistance to shear force.

Thus in one embodiment the oral care composition may be substantially free of phosphate source. This is especially preferred when the composition is a monophase hydrous composition (i.e. comprises greater than 1.5% water, preferably greater than 5% water, more preferably greater than 10% water and most preferably from 20 to 90% water by weight of the composition). Presence of calcium silicate, composite particles and phosphate sources in a monophase hydrous formulation can lead to premature reaction of the calcium and phosphate and instability of the product.

For certain compositions, especially anhydrous compositions (i.e. compositions substantially free from water) or dual phase hydrous compositions, it is preferable to compound a phosphate source in the oral composition to aid in situ generation of calcium phosphate.

The phosphate source that may be used in this invention is limited only to the extent that the same may be used in a composition suitable for use in the mouth. Illustrative examples of the types of phosphate source suitable for use in this invention include trisodium phosphate, monosodium dihydrogen phosphate, disodium hydrogen phosphate, sodium pyrophosphate, tetrasodium pyrophosphate, sodium hexametaphosphate, tripotassium phosphate, monopotassium dihydrogen phosphate, dipotassium hydrogen phosphate, mixtures thereof or the like. The phosphate source is preferably one which is water soluble.

When used, the phosphate source typically makes up from 0.5 to 22%, and preferably, from 2 to 18%, and most preferably, from 4 to 16% by weight of the oral care composition, based on total weight of the oral care composition and including all ranges subsumed therein. In a preferred embodiment, the phosphate source used is trisodium phosphate and monosodium dihydrogen phosphate at a trisodium phosphate to monosodium dihydrogen phosphate weight ratio of 1:4 to 4:1, preferably 1:3 to 3:1, and most preferably, from 1:2 to 2:1, including all ratios subsumed therein. In another preferred embodiment, the phosphate source used is or at least comprises monosodium dihydrogen phosphate.

The oral care composition preferably has a pH of greater than 5.0. If the pH of the composition is too low then it may lower the pH in the oral cavity such that generation of in situ calcium phosphate is retarded. Therefore, it is preferred that the pH of the oral care composition is in the range 5.5 to 11.0, more preferably 6.0 to 10.5 and most preferably 7.0 to 10.0.

The composition of the present invention is an oral care composition and typically comprises physiologically acceptable carrier. The carrier preferably comprises at least surfactant, thickener, humectant or a combination thereof.

Preferably the oral care composition comprises a surfactant. Preferably the composition comprises at least 0.01% surfactant by weight of the composition, more preferably at least 0.1% and most preferably from 0.5 to 7%. Suitable surfactants include anionic surfactants, such as the sodium, magnesium, ammonium or ethanolamine salts of $C_8$ to $C_{18}$ alkyl sulphates (for example sodium lauryl sulphate), $C_8$ to $C_{18}$ alkyl sulphosuccinates (for example dioctyl sodium sulphosuccinate), $C_8$ to $C_{18}$ alkyl sulphoacetates (such as sodium lauryl sulphoacetate), $C_8$ to $C_{18}$ alkyl sarcosinates (such as sodium lauryl sarcosinate), $C_8$ to $C_{18}$ alkyl phosphates (which can optionally comprise up to 10 ethylene oxide and/or propylene oxide units) and sulphated monoglycerides. Other suitable surfactants include nonionic surfactants, such as optionally polyethoxylated fatty acid sorbitan esters, ethoxylated fatty acids, esters of polyethylene glycol, ethoxylates of fatty acid monoglycerides and diglycerides, and ethylene oxide/propylene oxide block polymers. Other suitable surfactants include amphoteric surfactants, such as betaines or sulphobetaines. Mixtures of any of the above described materials may also be used. More preferably the surfactant comprises or is anionic surfactant. The preferred anionic surfactants are sodium lauryl sulphate and/or sodium dodecylbenzene sulfonate. Most preferably the surfactant is sodium lauryl sulphate.

Thickener may also be used in this invention and is limited only to the extent that the same may be added to a composition suitable for use in the mouth. Illustrative examples of the types of thickeners that may be used in this invention include, sodium carboxymethyl cellulose (SCMC), hydroxyl ethyl cellulose, methyl cellulose, ethyl cellulose, gum tragacanth, gum arabic, gum karaya, sodium alginate, carrageenan, guar, xanthan gum, Irish moss, starch, modified starch, silica based thickeners including silica aerogels, magnesium aluminum silicate (e.g., Veegum), Carbomers (cross-linked acrylates) and mixtures thereof.

Typically, sodium carboxymethyl cellulose and/or a Carbomer is/are preferred. When a Carbomer is employed, those having a weight-average molecular weight of at least 700,000 are desired, and preferably, those having a molecular weight of at least 1,200,000, and most preferably, those having a molecular weight of at least about 2,500,000 are desired. Mixtures of Carbomers may also be used herein.

In an especially preferred embodiment, the Carbomer is Synthalen PNC, Synthalen KP or a mixture thereof. It has been described as a high molecular weight and cross-linked polyacrylic acid and identified via CAS number 9063-87-0. These types of materials are available commercially from suppliers like Sigma.

In another especially preferred embodiment, the sodium carboxymethyl cellulose (SCMC) used is SCMC 9H. It has been described as a sodium salt of a cellulose derivative with carboxymethyl groups bound to hydroxy groups of glucopyranose backbone monomers and identified via CAS number 9004-32-4. The same is available from suppliers like Alfa Chem.

Thickener typically makes up from 0.01 to about 10%, more preferably from 0.1 to 9%, and most preferably, from 1.5 to 8% by weight of the oral care composition, based on total weight of the composition and including all ranges subsumed therein.

When the oral care composition of this invention is a toothpaste or gel, the same typically has a viscosity from about 30,000 to 180,000 centipoise, and preferably, from 60,000 to 170,000 centipoise, and most preferably, from 65,000 to 165,000 centipoise.

Suitable humectants are preferably used in the oral care composition of the present invention and they include, for example, glycerin, sorbitol, propylene glycol, dipropylene glycol, diglycerol, triacetin, mineral oil, polyethylene glycol (preferably, PEG-400), alkane diols like butane diol and hexanediol, ethanol, pentylene glycol, or a mixture thereof. Glycerin, polyethylene glycol, sorbitol or mixtures thereof are the preferred humectants.

The humectant may be present in the range of from 10 to 90% by weight of the oral care composition. More preferably, the carrier humectant makes up from 25 to 80%, and most preferably, from 45 to 70% by weight of the composition, based on total weight of the composition and including all ranges subsumed therein.

The oral care composition of the present invention may contain a variety of other ingredients which are common in the art to enhance physical properties and performance. These ingredients include antimicrobial agents, anti-inflammatory agents, anti-caries agents, plaque buffers, fluoride sources, vitamins, plant extracts, desensitizing agents, anti-calculus agents, biomolecules, flavors, proteinaceous materials, preservatives, opacifying agents, coloring agents, pH-adjusting agents, sweetening agents, particulate abrasive materials, polymeric compounds, buffers and salts to buffer the pH and ionic strength of the compositions, and mixtures thereof. Such ingredients typically and collectively make-up less than 20% by weight of the composition, and preferably, from 0.0 to 15% by weight, and most preferably, from 0.01 to 12% by weight of the composition, including all ranges subsumed therein.

The oral care composition of this invention can be used in a method of whitening the teeth of an individual comprising applying the composition to at least one surface of the teeth of the individual. Additionally, the oral care composition may be used in a method of remineralizing the teeth of an individual comprising applying the composition to at least one surface of the teeth of the individual. The oral care composition of this invention may additionally or alternatively be for use as a medicament and/or used in the manufacture of a medicament for providing an oral care benefit as described herein, such as for increasing the whiteness of the teeth of an individual.

Typically the composition will be packaged. In tooth paste or gel form, the composition may be packaged in a conventional plastic laminate, metal tube or a single compartment dispenser. The same may be applied to dental surfaces by any physical means, such as a toothbrush, fingertip or by an applicator directly to the sensitive area. In liquid mouthwash form the composition may be packaged in a bottle, sachet or other convenient container.

The composition can be effective even when used in an individual's daily oral hygiene routine. For example, the composition may be brushed onto the teeth and/or be rinsed around the inside of the mouth of the individual. The composition may, for example, be contacted with the teeth for a time period of one second to 20 hours. More preferably from 10 s to 10 hours, more preferably still from 30 s to 1 hour and most preferably from 1 minute to 5 minutes. The composition may be used daily, for example for use by an individual once, twice or three times per day.

The following examples are provided to facilitate an understanding of the present invention. The examples are not provided to limit the scope of the claims.

EXAMPLES

Oral care compositions consistent with this invention were prepared according to the formulations detailed in Table 1. All ingredients are expressed by weight percent of the total formulation, and as level of active ingredient.

TABLE 1

| Ingredient | Sample 1 | Sample 2 | Sample 3 | Sample 4 | Sample 5 |
|---|---|---|---|---|---|
| Sorbitol | 60.0 | 55.0 | 65.0 | 50 | 35 |
| PEG-1500 | 2.0 | 2.0 | 2.0 | 2.0 | 2.0 |
| NaF | 0.32 | 0.32 | 0.32 | 0.32 | 0.32 |
| Sodium Saccharine | 0.25 | 0.25 | 0.25 | 0.25 | 0.25 |
| Sodium lauryl sulfate | 1.98 | 1.98 | 1.98 | 1.98 | 1.98 |
| Flavor | 1.00 | 1.00 | 1.00 | 1.00 | 1.00 |
| Abrasive silica | 6.00 | 6.00 | 6.00 | 6.00 | 6.00 |
| Thickening silica | 7.00 | 7.00 | 7.00 | 7.00 | — |
| Sodium carboxymethyl cellulose | 0.55 | 0.55 | 0.55 | 0.55 | — |
| Calcium silicate hydrate | — | 5.00 | 5.00 | 10.00 | 30.00 |
| Calcium silicate coated titanium dioxide[a] | 10 | 10 | — | 10.00 | 10.00 |
| Water | Balance | Balance | Balance | Balance | Balance |

[a]Calcium silicate coated titanium dioxide was prepared according to WO 2012/031785A

Example 1

This example demonstrates the improvement of tooth whitening effect by using high refractive index composite particles in the presence of calcium silicate hydrate (CSH).

Preparation of Calcium Silicate Hydrate Powder

The calcium silicate hydrate (CSH) was prepared using a mixture of calcium hydroxide and sodium silicate in deionised water. The mixture was formed with an initial Ca:Si ratio of 1:2. The mixture was continuously stirred at room temperature (25° C.). The pH of the reaction mixture was adjusted to and maintained around 11 using hydrochloric acid. After stirring for 5 hours the reaction mixture was filtered and the cake washed three times with water before again being filtered. The filter cake was dried in an oven at 80° C. for 12 hours to yield the final CSH powder.

Methods

To investigate the whitening effect of the samples, the following in vitro test was performed. Changes in whiteness just after the tooth brush with toothpaste in the morning is recorded as instant tooth whitening effect, and changes in whiteness after water brushing, which mimics breakfast, is recorded as long-lasting tooth whitening effect. The measurement is carried out using a Konica Minolta-2600D colorimeter. The WIO index is an index which has been optimized specifically for the evaluation of whiteness in teeth (as described in Journal of Dentistry, volume 36, Supplement 1, 2008, pages 2 to 7).

The bovine tooth blocks were treated with different toothpaste via brushing following the same protocol. At the start point, toothpaste was made into slurry by mixing toothpaste and water. The tooth blocks were brushed with the fresh toothpaste slurry under a tooth brushing machine equipped with toothbrushes. The load of the tooth brushing was 170 g+/−5 g and the automatic brushing operated at a speed of 150 rpm. After brushing for 1 min, the tooth blocks were rinsed with distilled water and soaked in simulated oral fluid (SOF) under the condition of a shaking water bath at 37° C. and 60.0 rpm. After soaking for 3 to 4 hours, the tooth blocks were brushed with water by machine using the same procedure as brushing with toothpaste to mimic lunch. The tooth blocks were soaked in SOF again for 3 to 4 hours before water brushing again to mimic supper then the tooth blocks were brushed with toothpaste following the same procedure as in the first step. The tooth blocks were kept in SOF overnight in a shaking water bath at 37° C. to mimic oral environment. At the end point, the tooth blocks were water brushed again to mimic breakfast. These steps are considered as a whole treatment cycle within one day. The tooth blocks were treated for 42 cycles in total to mimic six weeks of twice daily tooth brushing. During the experiment, the tooth colour was monitored at both start and end points every day. After four weeks treatment, the tooth colour was monitored every two days. The changes in WIO values (ΔWIO) from baseline were calculated and statistically analyzed.

Simulated oral fluid was made by combining the ingredients in Table 2:

TABLE 2

| Ingredient | Amount/g |
|---|---|
| NaCl | 16.07 |
| NaHCO$_3$ | 0.7 |
| KCl | 0.448 |
| K$_2$HPO$_3$*H$_2$O | 3.27 |
| MgCl$_2$*6H$_2$O | 0.622 |
| 1M HCl | 40 ml |
| CaCl$_2$ | 0.1998 |
| Na$_2$SO$_4$ | 0.1434 |
| Buffer | Adjust pH to 7.0 |
| Water | Balance to 2 L |

Results

The results of both instant whitening and long-lasting whitening effect after certain period of time of treatment are summarized in Table 3 and Table 4, respectively (error represents 95% confidence interval for duplicate measurements).

TABLE 3

| Change in WIO (Instant tooth whitening) | Sample A | Sample 1 | Sample 2 | Sample 3 | Sample 4 | Sample 5 |
|---|---|---|---|---|---|---|
| One week | −1.33 ± 0.875 | 3.01 ± 1.272 | 4.62 ± 2.413 | 2.21 ± 1.424 | 0.29 ± 1.108 | |
| Two weeks | −0.61 ± 0.818 | 3.20 ± 1.064 | 5.70 ± 1.292 | 3.58 ± 1.505 | 0.05 ± 1.465 | |
| Four weeks | −0.90 ± 1.191 | 4.26 ± 2.220 | 6.14 ± 1.765 | 4.85 ± 2.484 | 0.90 ± 1.150 | |
| Six weeks | −0.49 ± 0.988 | 3.87 ± 1.416 | 6.29 ± 1.083 | 5.66 ± 2.040 | 0.32 ± 1.089 | |

TABLE 4

| Change in WIO (Long-lasting tooth whitening) | Sample A | Sample 1 | Sample 2 | Sample 4 | Sample 5 |
|---|---|---|---|---|---|
| One week | −0.82 ± 0.866 | −0.41 ± 0.771 | 1.65 ± 1.354 | 0.12 ± 1.690 | −0.42 ± 0.716 |
| Two weeks | −1.23 ± 0.891 | −0.79 ± 1.373 | 2.27 ± 1.527 | 0.417 ± 1.161 | −1.02 ± 0.934 |
| Four weeks | −0.89 ± 1.221 | 0.15 ± 1.067 | 2.480 ± 0.927 | 1.03 ± 1.453 | 0.38 ± 1.535 |
| Six weeks | 0.06 ± 0.983 | 0.66 ± 1.863 | 3.77 ± 1.494 | 2.04 ± 1.507 | 0.19 ± 0.948 |

Sample A is a comparative example using commercial toothpaste. In all cases, Samples 1, 2 and 4 showed significantly better instant tooth whitening effect than comparative Sample A. But Sample 5 comprising CSH and composite particles in a relative weight ratio of 3:1 showed no instant tooth whitening effect.

In regards to long-lasting tooth whitening effect, Sample 2 and Sample 4 comprising both CSH and composite particles had significantly better performance compared to Sample 1, Sample 5 and Sample A, which had no long-lasting tooth whitening effect. Sample 3 comprising only CSH had also been compared to comparative Sample A, and showed no instant tooth whitening effect as shown in Table 5 (error represents 95% confidence interval for duplicate measurements).

TABLE 5

| Change in WIO (instant tooth whitening) | Sample A | Sample 3 |
|---|---|---|
| After one toothpaste brushing | −0.04 ± 0.357 | 0.82 ± 1.140 |

After six weeks of twice daily brushing, SEM (Scanning Electron Microscopy) images of the enamel block surface were taken. From corresponding cross-section SEM images, it appeared that the enamel block treated with Sample 2 showed the formation of a new layer on the surface while the one treated with Sample 1 did not have a new layer formed. Analysis using EDX (Energy Dispersive X-ray Spectroscopy) identified the elements of Ti, Si, Ca and P within the new layer, indicating the deposition of composite particles on tooth surface.

Example 2

This example demonstrates the effect of relative weight ratio of calcium silicate to composite particles on the tooth whitening effect.

Methods

To investigate the whitening effect of the samples, the following in vitro test was performed. Changes in whiteness after water brushing, which mimics breakfast, is recorded as long-lasting tooth whitening effect.

The bovine tooth blocks were treated with different test samples via brushing following the same protocol. At the start point, test samples were made into slurry by mixing with water. The tooth blocks were brushed with the fresh slurry under a tooth brushing machine equipped with toothbrushes. The load of the tooth brushing was 170 g+/−5 g and the automatic brushing operated at a speed of 150 rpm. After brushing for 1 min, the tooth blocks were rinsed with distilled water and soaked in SOF under the condition of a shaking water bath at 37° C. and 60.0 rpm. After soaking for 3 to 4 hours, the tooth blocks were brushed with water by machine for 1 min, then the tooth blocks were brushed again with the slurry of the test samples using the same procedure as in the first step. The tooth blocks were soaked in SOF again for 3 to 4 hours before brushing with water again to mimic supper then the tooth blocks were brushed with the slurry of the test samples following the same procedure as in the first step. The tooth blocks were kept in SOF overnight in a shaking water bath at 37° C. to mimic oral environment. At the end point, the tooth blocks were water brushed again to mimic breakfast. These steps are considered as a whole treatment cycle within one day. The tooth blocks were treated for 28 cycles in total to mimic four weeks of three times daily tooth brushing. During the experiment, the tooth colour was monitored at the end point every day. The changes in WIO values from baseline were calculated and statistically analyzed in Table 7 (error represents 95% confidence interval for duplicate measurements).

TABLE 6

| Ingredient | Sample 6 | Sample 7 | Sample 8 |
|---|---|---|---|
| Calcium silicate[b] | 5 | 10 | 30 |
| Calcium silicate coated titanium dioxide[a] | 10 | 10 | 10 |
| Glycerin | Balance | Balance | Balance |

[b]Commercially available calcium silicate (CaSiO₃) from P.Q. company (Sorbosil CA40)

TABLE 7

| Change in WIO (Long-lasting tooth whitening) | Sample 6 | Sample 7 | Sample 8 |
|---|---|---|---|
| One week | 0.91 ± 2.555 | −0.14 ± 1.518 | −0.03 ± 0.767 |
| Two weeks | 1.80 ± 4.187 | 1.93 ± 2.292 | −0.11 ± 1.151 |
| Four weeks | 2.76 ± 3.995 | 2.98 ± 2.603 | 0.46 ± 0.720 |

It can be seen that the relative weight ratio of calcium silicate to composite particles is important to the tooth whitening effect. Sample 6 and Sample 7 having a smaller ratio of calcium silicate to composite particles showed significantly improved long-lasting tooth whitening effect, while there was no such effect observed in Sample 8.

The invention claimed is:
1. An oral care composition comprising:
   a) calcium silicate; and
   b) high refractive index composite particles having diameters of 10 nm to less than 50 microns, wherein the high refractive index composite particle comprises a first component core and a second component coating comprising calcium silicate;
   wherein the first component core comprises a metal salt selected from the group consisting of zinc oxide, titanium dioxide, zirconium dioxide, and a mixture thereof;
   wherein the refractive index of the composite particles is in the range from 1.9 to 4.0; and wherein the calcium silicate and high refractive index composite particles are present in a weight ratio (a:b) of 1:10 to 2:1.

2. The oral care composition according to claim 1, wherein the calcium silicate of component (a) is calcium silicate hydrate which comprises water of hydration in an amount of from 5 to 50% by weight of the calcium silicate hydrate.

3. The oral care composition according to claim 1, wherein the calcium silicate of component (a) is present in an amount from 0.1 to 50% by weight of the composition.

4. The oral care composition according to claim 3, wherein the calcium silicate of component (a) is present in an amount from 1 to 20% by weight of the composition.

5. The oral care composition according to claim 1, wherein the refractive index of the composite particles is in the range from 2.5 to 3.0.

6. The oral care composition according to claim 1, wherein the second component coating further comprises an element selected from the group consisting of potassium, sodium, magnesium, aluminum and a mixture thereof.

7. The oral care composition according to claim 1, wherein the first component core of high refractive index composite particle is titanium dioxide.

8. The oral care composition according to claim 1, wherein the high refractive index composite particle is present in an amount from 0.25 to 60% by weight of the composition.

9. The oral care composition according to claim 8, wherein the high refractive index composite particle is present in an amount from 1 to 30% by weight of the composition.

10. The oral care composition according to claim 1, wherein the relative weight ratio of calcium silicate to high refractive index composite particles ranges from 1:3 to 2:1.

11. The oral care composition according to claim 1, wherein the composition is substantially free of phosphate source.

12. A method for whitening the teeth of an individual comprising applying the composition as claimed in claim 1 to at least one surface of the teeth of the individual.

13. A process for manufacturing the oral care composition as claimed in claim 1 wherein the process comprises the steps of:
   i) manufacturing high refractive index composite particles;
   ii) mixing the composite particles with calcium silicate to form the oral care composition.

14. An oral care composition comprising:
   a) calcium silicate; and
   b) high refractive index composite particles, wherein the high refractive index composite particles comprise a first component core and a second component coating,
   wherein the first component core is titanium dioxide and the second component coating is calcium silicate;
   wherein the refractive index of the composite particles is in the range from 1.9 to 4.0;
   wherein the calcium silicate and high refractive index composite particles are present in a weight ratio (a:b) of 1:10 to 2:1.

15. The oral care composition according to claim 14, wherein the high refractive index composite particle is present in an amount from 0.25 to 60% by weight of the composition.

16. The oral care composition according to claim 14, wherein the high refractive index composite particle is present in an amount from 1 to 30% by weight of the composition.

17. The oral care composition according to claim 16, wherein the relative weight ratio of calcium silicate to high refractive index composite particles ranges from 1:3 to 2:1.

* * * * *